(12) United States Patent
Merassi et al.

(10) Patent No.: US 9,486,593 B2
(45) Date of Patent: *Nov. 8, 2016

(54) PROCESS FOR MANUFACTURING AN INTEGRATED MEMBRANE OF NOZZLES IN MEMS TECHNOLOGY FOR A SPRAY DEVICE AND SPRAY DEVICE USING SUCH MEMBRANE

(71) Applicant: STMicroelectronics S.r.l., Agrate Brianza (IT)

(72) Inventors: Angelo Antonio Merassi, Vigevano (IT); Angelo Pesci, Agrate Brianza (IT); Benedetto Vigna, Pietrapertosa (IT); Ernestino Galeazzi, Corbetta (IT); Marco Mantovani, Lainate (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 340 days.

This patent is subject to a terminal disclaimer.

(21) Appl. No.: 14/225,285

(22) Filed: Mar. 25, 2014

(65) Prior Publication Data

US 2014/0202453 A1    Jul. 24, 2014

Related U.S. Application Data

(60) Continuation of application No. 13/754,510, filed on Jan. 30, 2013, now Pat. No. 8,721,910, which is a division of application No. 12/645,380, filed on Dec. 22, 2009, now abandoned.

(30) Foreign Application Priority Data

Dec. 23, 2008   (IT) ............................. TO2008A0980

(51) Int. Cl.
 *A61M 15/00*   (2006.01)
 *B05B 1/14*   (2006.01)
(Continued)

(52) U.S. Cl.
 CPC .............. *A61M 15/009* (2013.01); *B05B 1/14* (2013.01); *B05B 17/0638* (2013.01); *B05D 7/00* (2013.01);
(Continued)

(58) Field of Classification Search
 CPC ............. A01K 11/005; A01K 13/003; A61M 11/001; A61M 11/06; A61M 15/0003; A61M 15/0048; A61M 15/0065; A61M 15/0066; A61M 15/008; A61M 15/0085; A61M 15/009; A61M 15/02; A61M 15/025; A61M 2205/52; A61M 31/002; A61M 35/003; A61M 37/00; A61M 37/0084; B05B 1/005; B05B 1/14; B05B 1/24; B05B 12/085; B05B 15/02; B05B 17/0638; B05B 17/0646; B05B 7/0408; B05B 7/0433; B05B 7/0458; B05B 7/0475; B05B 7/00; B41J 2/16505; B41J 2/16535; B41J 3/36; B41J 3/407; B81B 2201/058; B81B 2203/0127; B81C 1/00087; F23D 11/104; Y10T 29/49401
 USPC ............ 128/200.14, 200.16, 200.18, 200.21, 128/200.23; 216/83, 95, 99; 239/102.2, 239/370, 4, 418, 690; 604/304, 310
 See application file for complete search history.

(56) References Cited

U.S. PATENT DOCUMENTS 6,196,219 B1   3/2001   Hess et al.
6,405,934 B1   6/2002   Hess et al.
(Continued)

*Primary Examiner* — Annette Dixon
(74) *Attorney, Agent, or Firm* — Seed IP Law Group LLP

(57) ABSTRACT

A process for manufacturing a membrane of nozzles of a spray device, comprising the steps of laying a substrate, forming a membrane layer on the substrate, forming a plurality of nozzles in the membrane layer, forming a plurality of supply channels in the substrate, each supply channel being substantially aligned in a vertical direction to a respective nozzle of the plurality of nozzles and in direct communication with the respective nozzle.

20 Claims, 5 Drawing Sheets

(51) Int. Cl.
   *B05B 17/00* (2006.01)
   *B81C 1/00* (2006.01)
   *B05D 7/00* (2006.01)

(52) U.S. Cl.
   CPC ...... *B81C 1/00087* (2013.01); *B81B 2201/058* (2013.01); *B81B 2203/0127* (2013.01); *Y10T 29/49401* (2015.01)

(56) References Cited

U.S. PATENT DOCUMENTS

| | | | |
|---|---|---|---|
| 7,726,303 B2* | 6/2010 | Tyvoll | A61M 15/0065 128/200.21 |
| 8,721,910 B2* | 5/2014 | Merassi | B05B 1/14 216/83 |
| 2003/0065294 A1* | 4/2003 | Pickup | A01K 11/005 604/304 |
| 2003/0080214 A1 | 5/2003 | Hess et al. | |
| 2004/0155943 A1 | 8/2004 | Kim et al. | |
| 2004/0195352 A1 | 10/2004 | Koerner et al. | |
| 2005/0030338 A1 | 2/2005 | Silverbrook | |
| 2005/0150489 A1* | 7/2005 | Dunfield | A61M 15/0065 128/200.14 |
| 2005/0270334 A1 | 12/2005 | Silverbrook et al. | |
| 2006/0169800 A1* | 8/2006 | Rosell | A61M 11/06 239/418 |
| 2006/0176338 A1 | 8/2006 | Deguchi et al. | |
| 2010/0045736 A1 | 2/2010 | Bernard et al. | |

\* cited by examiner

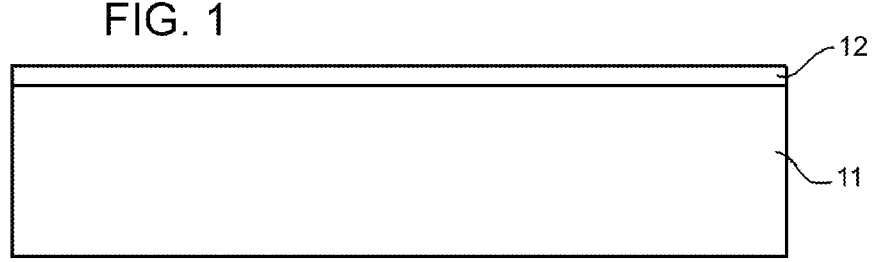
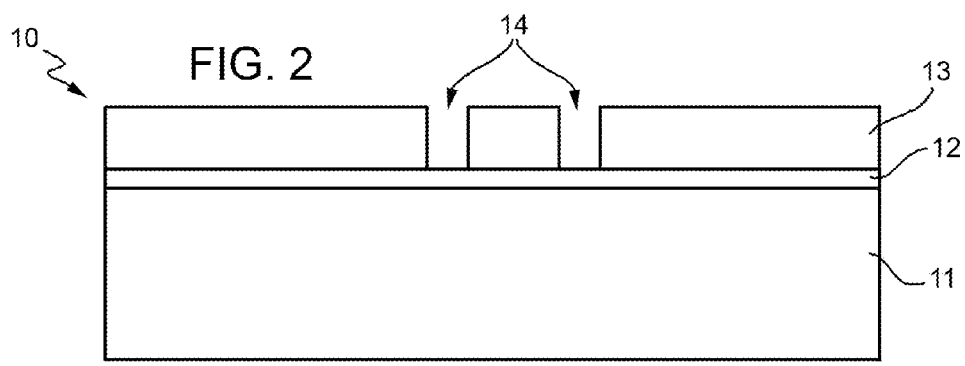
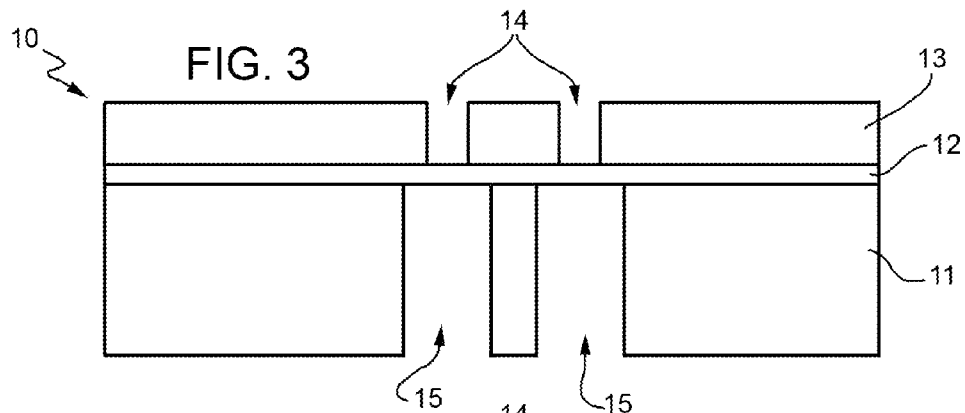
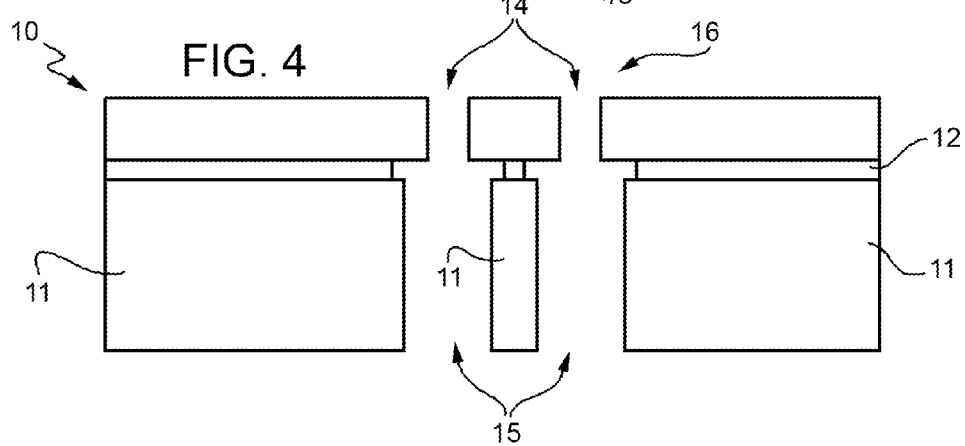

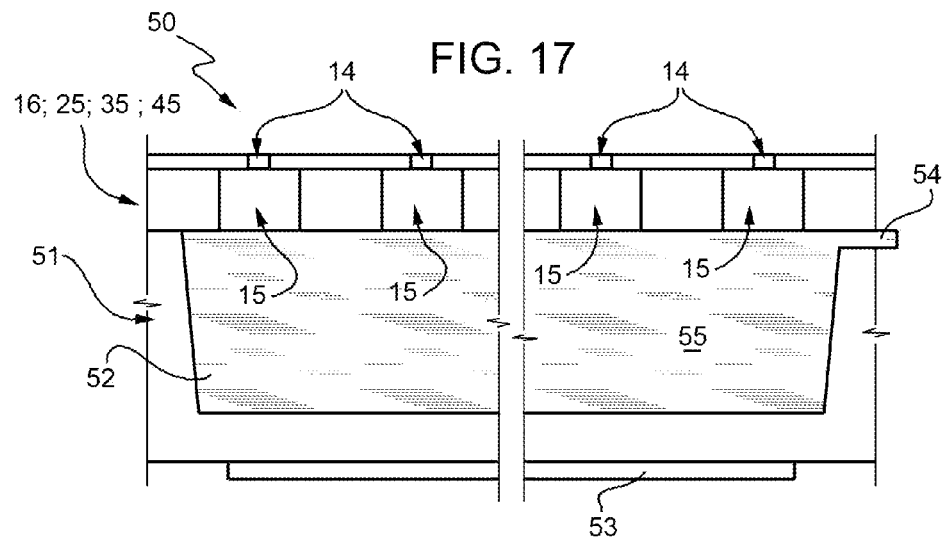
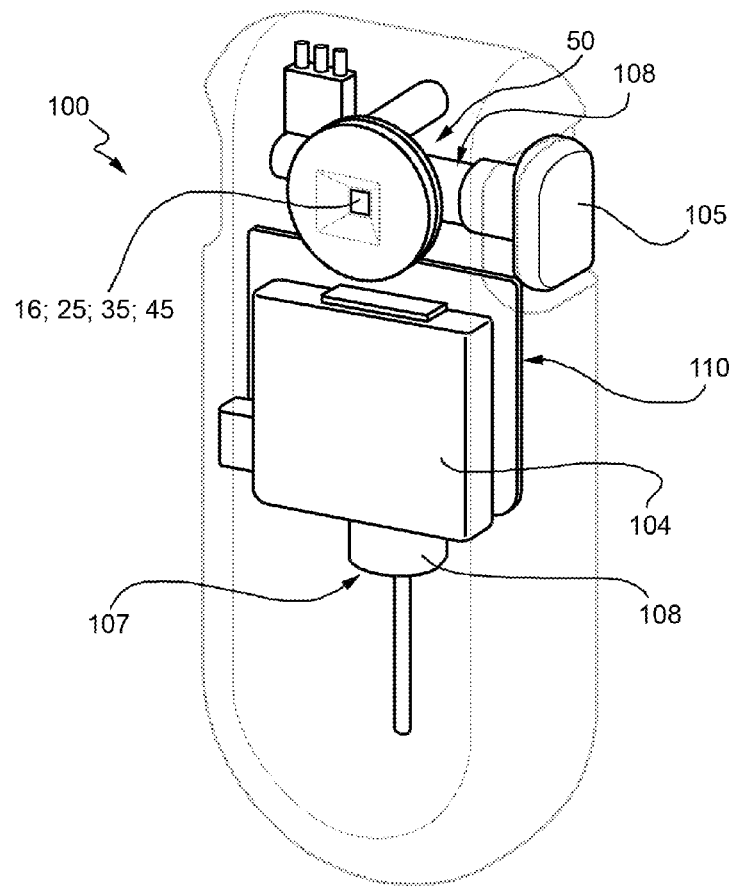

PROCESS FOR MANUFACTURING AN INTEGRATED MEMBRANE OF NOZZLES IN MEMS TECHNOLOGY FOR A SPRAY DEVICE AND SPRAY DEVICE USING SUCH MEMBRANE

BACKGROUND

1. Technical Field

The present disclosure relates to a process for manufacturing an integrated membrane of nozzles in MEMS technology for a spray device, and to the spray device that uses such membrane, in particular a spray or aerosol device of an inhaler used for administration of pharmaceutical products, parapharmaceutical products, or perfumes.

2. Description of the Related Art

For example, in applications in the medical field, inhalers of a known type are generally used for administering medicaments in controlled doses or for a wide range of aerosol-based therapies.

An inhaler supplies the medicament, which is in liquid form, as a nebulized dispersion of drops. Preferably, an inhaler is of contained dimensions and generally operated with a battery so that the patient is able to carry it with him and use it in a discrete way.

Inhalers of a known type, for example, of the type described in U.S. Pat. No. 6,196,219, generally comprise a membrane provided with nozzles (or pores) and set facing a reservoir containing the liquid to be nebulized. An actuation element, for example, a piezoelectric actuation element, can be used for deforming the reservoir and causing exit of the liquid through the nozzles of the membrane.

As is known, the effectiveness of a medical treatment depends upon the activity of the active principle, and said effectiveness depends in turn upon the amount of each dose of medicament nebulized and upon the point of impact of the spray. Consequently, the amount of nebulized liquid and the directionality of each spray should be as constant as possible for different sprays, so as to maximize the effectiveness of the medical therapy.

It is clear that the type of membrane of nozzles and the size and shape of the nozzles, as well as the uniformity of the size and shape of the nozzles, are parameters that are particularly important to define the size and directionality of the drops generated and their reproducibility.

Various membranes of nozzles for inhalers have been proposed; however, some of these require a particularly complex manufacturing process, whilst others do not enable a high reproducibility of the nozzles.

BRIEF SUMMARY

One embodiment is a process for manufacturing an integrated membrane of nozzles obtained with MEMS technology for a spray device, and the spray device that uses said membrane that is free from the drawbacks of the known art.

Provided according to the present disclosure are a process for manufacturing an integrated membrane of nozzles obtained with MEMS technology for a spray device and the spray device that uses said membrane. In one embodiment, the process includes providing a substrate; forming a membrane layer on the substrate; forming a plurality of nozzles in the membrane layer; and forming a plurality of supply channels in the substrate. Each supply channel is substantially aligned in a vertical direction with a respective nozzle of said plurality of nozzles and is in direct communication with the respective nozzle

BRIEF DESCRIPTION OF THE SEVERAL VIEWS OF THE DRAWINGS

For a better understanding of the present disclosure preferred embodiments thereof are now described, purely by way of non-limiting example, with reference to the attached drawings, wherein:

FIGS. 1-4 show a cross-sectional view of a membrane of nozzles according to one embodiment of the present disclosure;

FIG. 17 shows a spray device that incorporates a membrane of nozzles according to any of the embodiments of the present disclosure; and FIG. 18 shows an inhaler that incorporates the spray device of FIG. 17.

DETAILED DESCRIPTION

Figure 5:
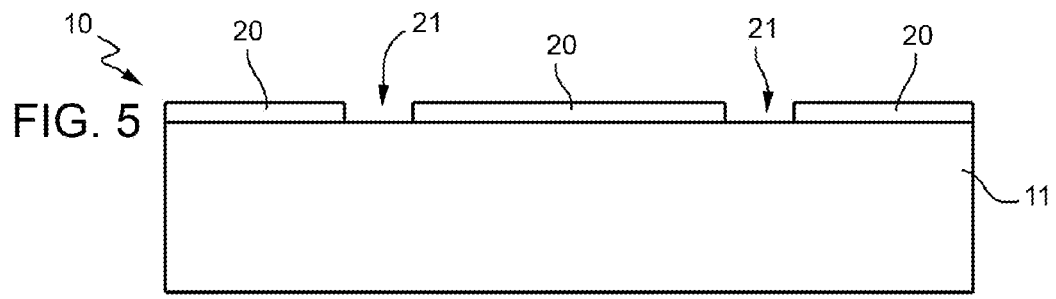
FIGS. 5-8 show a cross-sectional view of a membrane of nozzles according to another embodiment of the present disclosure.

As is shown in FIG. 1, according to one embodiment of the present disclosure, a wafer 10 is provided, comprising a substrate 11 made, for example, of silicon of an N type having a thickness of between 400 µm and 725 µm, preferably 400 µm. A sacrificial layer 12 is then laid, made, for example, of silicon oxide, which has a thickness of between 0.6 µm and 1.5 µm, preferably 0.8 µm.

Next (FIG. 2), grown on the wafer 10 is a membrane layer 13, preferably made of non-doped polysilicon. Alternatively, the membrane layer 13 may be made of deposited material, compatible with silicon processing technology (e.g., deposited polysilicon). Providing a membrane layer 13 made of grown or deposited material (thus differing from the substrate in either material and/or crystalline structure) has the advantage that the choice of the material to be used may be tuned according to the particular application of the membrane layer 13. In fact, by varying the material of the membrane layer 13, the properties of the membrane layer 13 are varied (e.g., its elasticity, compatibility with biological materials, etc.).

The membrane layer 13 is then planarized until a final thickness is reached of between 1.5 µm and 10 µm, preferably 5 µm, and defined, for example, by means of dry etching so as to form a plurality of nozzles 14 (just two nozzles 14 are shown in the figure). Each nozzle 14 has preferably, in top plan view, a circular shape with a diameter of between 1 µm and 5 µm, according to the liquid that is to be used, and extends in depth throughout the thickness of the membrane layer 13.

Then (FIG. 3), a step of grinding of the back of the substrate 11 enables reduction of the thickness of the substrate down to approximately 400 µm. This step is not necessary in the case where the starting substrate 11 already has a thickness of 400 µm or less.

Next, formed in the substrate 11, preferably by means of a dry etch, are supply channels 15, each in a position corresponding, and substantially aligned vertically, to a respective nozzle 14. The supply channels 15 preferably have, in top plan view, a circular shape with a diameter of between 10 μm and 100 μm, preferably 40 μm, and extend in depth throughout the thickness of the substrate 11.

Finally (FIG. 4), the sacrificial layer 12 is partially removed, for example, by means of a wet etching of the buffered-oxide-etching (BOE) type so as to set in direct communication each nozzle 14 with the respective underlying supply channel 15.

A membrane of nozzles 16 is thus obtained, provided with a plurality of nozzles 14 (for example, 3200 nozzles uniformly distributed on a membrane having an area of approximately 25 mm²) that can be used in a spray device.

The process described with reference to FIGS. 1-4 enables formation of nozzles 14 and supply channels 15 all having respective uniform dimensions, hence guaranteeing high reproducibility, ease of production process, and extremely contained production costs.

The step of removal of the sacrificial layer 12, in particular if performed by means of wet etching, is important on account of a possible lateral overetching of the portions of sacrificial layer 12, which could cause an excessive weakening of portions of the membrane of nozzles 16 comprised between contiguous nozzles and consequent yielding of the membrane of nozzles 16 itself.

In order to overcome said drawback, according to a further embodiment of the present disclosure, the sacrificial layer 12, after being deposited, is defined so as to form portions isolated from one another of sacrificial layer 12 in positions corresponding to the areas in which it is envisaged to form the nozzles 14. In greater detail, as shown in FIG. 5, the sacrificial layer 12, after being deposited on the substrate 11, is defined so as to form sacrificial isles 20 separated from one another by means of trenches 21. Then (FIG. 6), in a way similar to what has been described with reference to FIG. 2, the membrane layer 13 is grown and is defined, thus providing a nozzle 14 in an area corresponding to each sacrificial isle 20. In particular, in this case, the membrane layer 13 is formed also inside the trenches 21, thus providing membrane anchorages 22 for anchoring the membrane layer 13 directly to the substrate 11.

After an optional step of grinding of the back of the substrate 11 to reduce the thickness thereof down to approximately 400 μm, the back of the substrate 11 is etched to form the supply channels 15.

Figure 8:
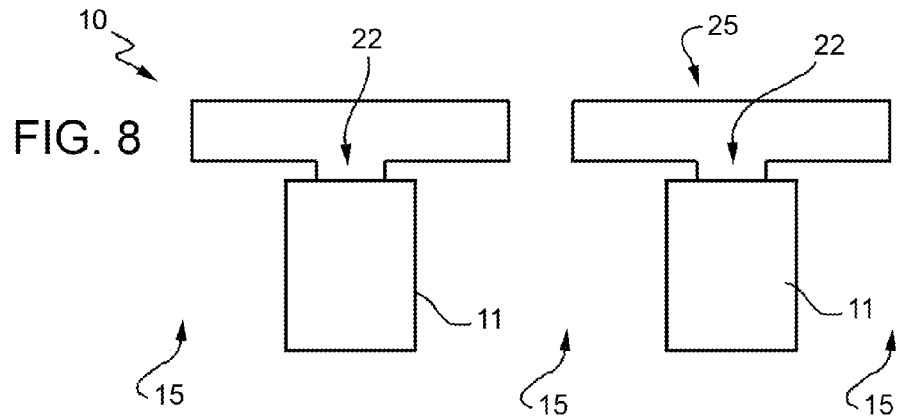
Figure 9:
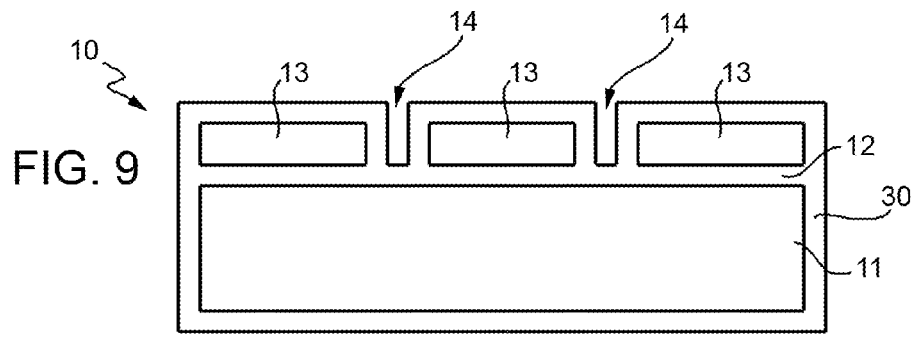
FIGS. 9-12 show a cross-sectional view of a membrane of nozzles according to a further embodiment of the present disclosure.
Figure 10:
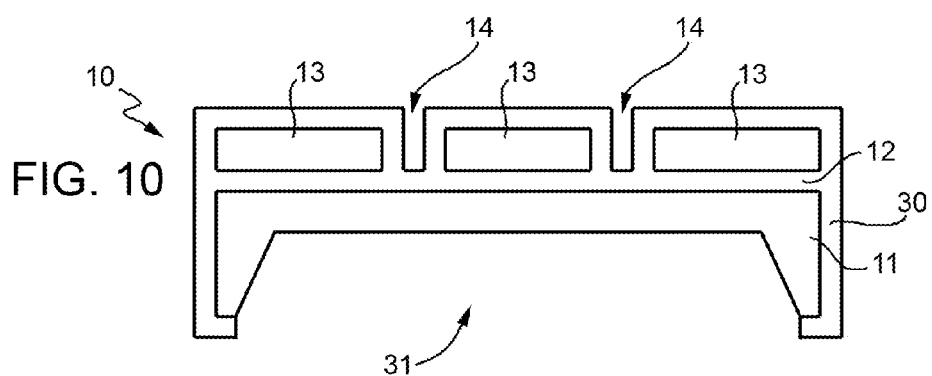
Figure 11:
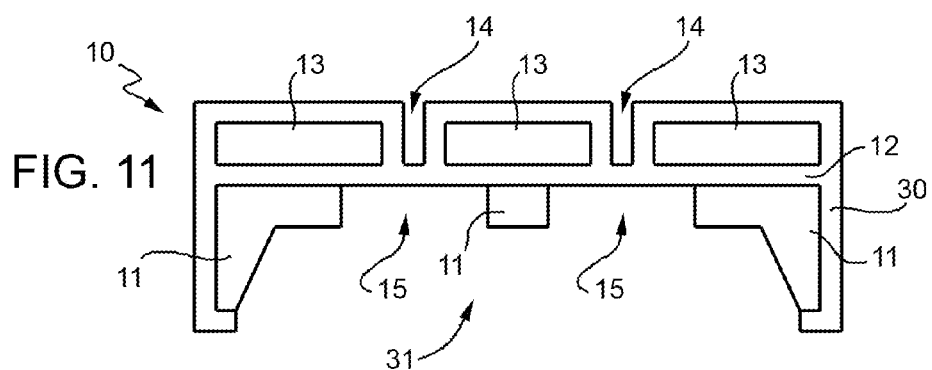
Figure 12:
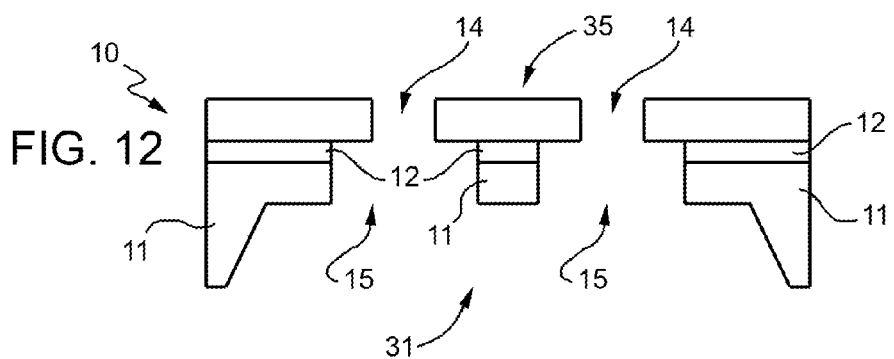
Figure 13:
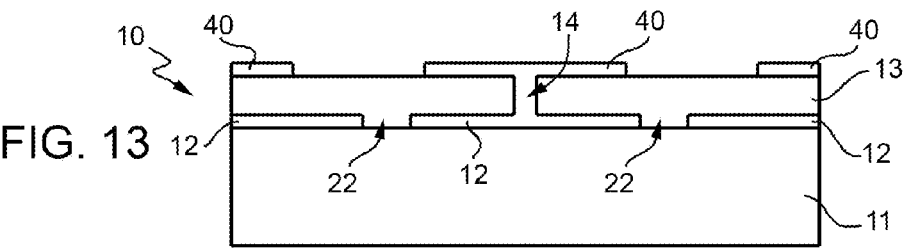
FIGS. 13-16 show a cross-sectional view of a membrane of nozzles according to another embodiment of the present disclosure.
Figure 14:
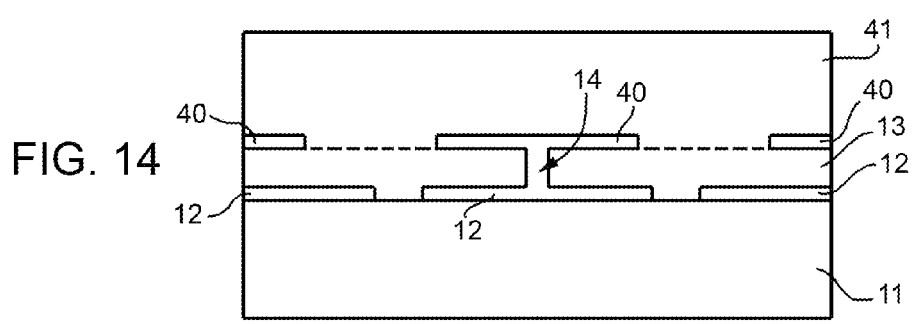
Figure 15:
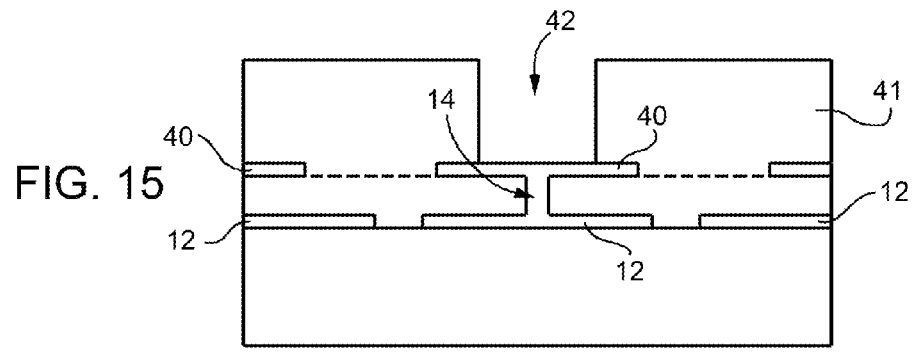
Figure 16:
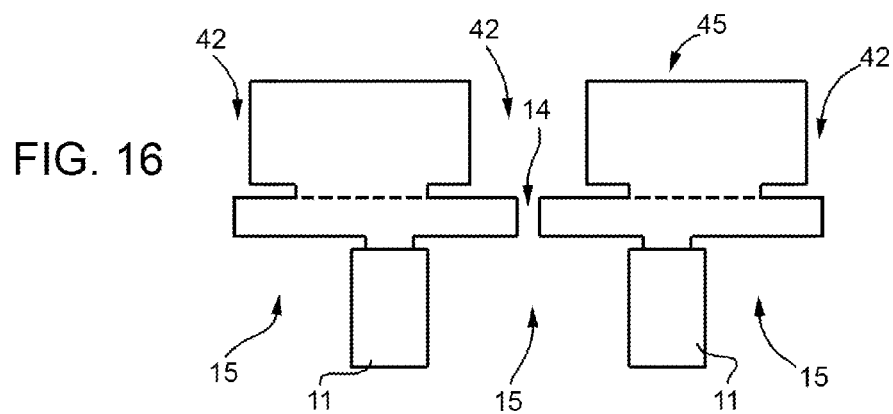

Finally (FIG. 8), the sacrificial isles 20 are removed by means of a wet etch, for example, with BOE, thus setting in direct contact each nozzle 14 with the respective supply channel 15 to form a membrane of nozzles 25.

According to this embodiment, a possible overetching of the oxide that forms the sacrificial isles 20 does not jeopardize the mechanical stability of the membrane 25 in so far as the membrane anchorages 22 are not damaged by the steps of the process described.

In order to reduce the overall dimensions of the spray device in which the membrane of nozzles is used, it may prove convenient to reduce the thickness of the substrate 11 and the depth of the supply channels 15 so that they can be coupled to other types of piezoelectrics. FIGS. 9-12 show the steps of the process of formation of a membrane of nozzles, according to a further embodiment.

In a way similar to what has been described previously, with reference to FIGS. 1 and 2, a wafer 10 is provided having a substrate 11 on which a sacrificial layer 12 is deposited and a membrane layer 13 is grown, in which nozzles 14 are obtained, for example, by means of dry etching.

After formation of the nozzles 14 (FIG. 9), the wafer 10 is protected by means of a protective layer 30, of a thickness of between 0.5 μm and 2 μm, preferably 1 μm, for example, made of thermally grown silicon oxide. In particular, the protective layer 30 also coats the internal walls and the bottom of the nozzles 14.

Then (FIG. 10), the protective layer 30 is removed from the back of the substrate 11 so as to create a window of a quadrangular shape underneath the plurality of nozzles 14. A subsequent etching step, for example, wet etching with the use of tetramethylammonium hydroxide (TMAH) enables selective removal of the substrate 11 where this is not protected by the protection layer 30 so as to provide a chamber 31, having a depth of between 100 μm and 400 μm. For example, in the case where the substrate 11 has a thickness of 400 μm, it is preferable to form a chamber 31 with a depth of 300 μm. During this etching step, the protective layer 30 performs the dual function of mask for definition of the shape of the chamber 31 and of protection for preventing an undesirable etching of the membrane layer 13.

Next (FIG. 11), a supply channel 15 is formed underneath each nozzle 14, by etching the substrate 11, for example, by means of a dry etch, until portions of the sacrificial layer 12 are exposed. Each supply channel 15 has a depth of between 50 μm and 300 μm. For example, in the case where the substrate 11 has a thickness of 400 μm and the chamber 31 a depth of 300 μm, each supply channel 15 will have a depth of 100 μm.

Finally (FIG. 12), the protective layer 30 and the portions of sacrificial layer 12 exposed are removed, for example, by means of wet etching of a BOE type, simultaneously providing a membrane of nozzles 35 comprising a portion of a reservoir (the chamber 31).

In some cases it may be preferable to envisage membranes of nozzles provided with elements for guiding jets that, in use, come out of each nozzle 14 so as to increase the directionality of the jet itself eliminating portions thereof having an angle of exit from the nozzle 14 greater than a certain maximum exit angle (assuming that each jet has a substantially conical shape). Membranes of nozzles of this type also prove to be more rigid.

For the above purpose, there may be envisaged formation of a guide channel, provided in a form integrated with the membrane of nozzles, set on each nozzle 14, according to a further embodiment.

Said further embodiment is described in what follows with reference to FIGS. 13-16.

Figure 6:
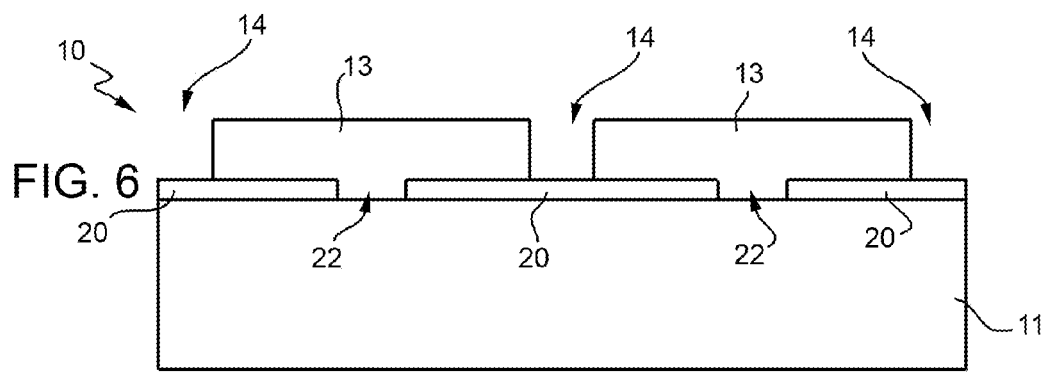
Figure 7:
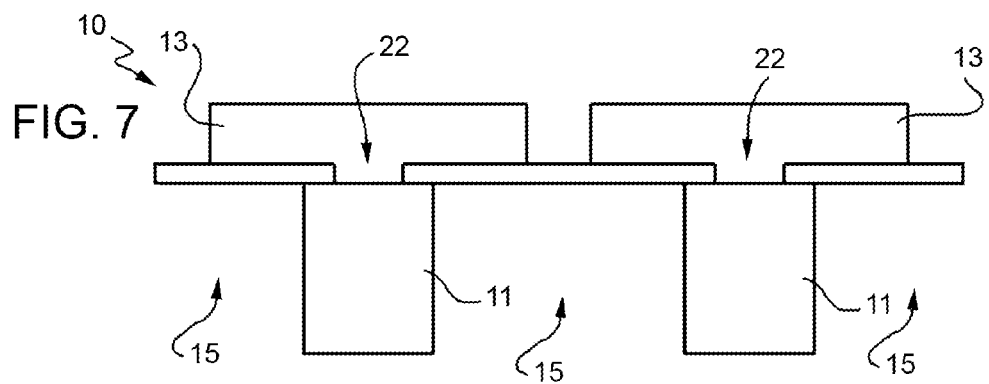

In a way similar to what has been described with reference to the embodiment of FIGS. 5 and 6, a wafer 10 is provided, comprising a substrate 11, on which a sacrificial layer 12 is deposited and defined and a membrane layer 13 is grown, anchored to the substrate 11 by means of membrane anchorages 22. The nozzles 14 are then formed by selectively removing portions of the membrane layer 13.

Next (FIG. 13), a shaping layer 40 is deposited, having a sacrificial function, so as to fill the nozzles 14 and form a layer on the membrane layer 13. The shaping layer 40 may be made, for example, of silicon oxide, having a thickness of between 0.2 μm and 1 μm, preferably 0.5 μm. The shaping layer 40 is defined so as to remove portions of the shaping layer 40 laterally staggered with respect to each nozzle 14, and kept in portions substantially aligned vertically to each nozzle 14.

Then (FIG. 14), a guide-channel layer 41 is formed on the wafer 10, for example, by epitaxial growth of silicon having a thickness of between 2 µm and 6 µm, preferably 5 µm.

Next (FIG. 15), the guide-channel layer 41 is defined so as to form a guide channel 42 on top of, and substantially aligned vertically to, each nozzle 14, having a preferably circular shape, a diameter of 5 µm, and a depth equal to the thickness of the guide-channel layer 41. In particular, the guide-channel layer 41 is selectively removed, for example, by means of dry etching, until the portions of the second sacrificial layer 40 arranged on the nozzles 14 are at least partially exposed.

Then (FIG. 16), the substrate 11 is etched from the back to form a supply channel 15 for each nozzle 14, in a way similar to what has been described with reference to the other embodiments illustrated.

A step of wet etching, for example, of the BOE type, enables removal of the portions of sacrificial layer 12 and of shaping layer 40 exposed in order to set in direct communication each supply channel 15 with the respective nozzle 14 and each guide channel 42 with the respective nozzle 14. In this way, the supply channel 15 and the guide channel 42 are in communication via the nozzle 14. A membrane of nozzles 45 is thus provided.

It is clear that, as the size and the depth of the guide channel 42 vary, the solid angle of the jet coming out of the guide channel 42 will vary accordingly. It is thus possible to provide membranes of nozzles equipped with guide channels 42 having different dimensions according to the desired directionality and amplitude of the jet, depending upon the use to which they will be put.

Furthermore, for simplicity, said embodiment has been described with preferred reference to the embodiment of FIGS. 5-8, in which the membrane is anchored to the substrate by means of the membrane anchorages 22. However, the process described for formation of the guide channels 42 may be applied, with obvious modifications, also to the other embodiments.

FIG. 17 shows a spray device 50 comprising a membrane of nozzles 16, 25, 35, or 45, provided according to any of the embodiments of the present disclosure.

The spray device 50 further comprises a reservoir 51, set underneath the membrane of nozzles 16, 25, 35, or 45 and designed to contain in an internal housing 52 of its own a liquid substance 55 (for example, a medicament), which, in use, comes out of the nozzles 14 through the supply channels 15. Actuation of the spray device 50 can be obtained in various ways, for example, by means of an actuator 53 of a piezoelectric type, fixed with respect to a bottom face of the reservoir 51 opposite to the membrane of nozzles 16, 25, 35 or 45. When activated by means of an appropriate control electronics (not shown), said actuator 53 induces a vibration that is transmitted through the reservoir 51 to the liquid contained in the housing 52, causing exit thereof through the nozzles 14.

Advantageously, an inlet mouth 54 can be provided for recharging the reservoir 51 with further liquid substance 55, when the liquid substance 55, following upon use of the spray device 50, runs out.

The spray device 50 can be incorporated in an inhaler 100, for controlled release of medicaments or anaesthetics.

The inhaler 100 can comprise an electronic controller 110, in turn comprising a control board, for controlling release of a precise amount of liquid medicament to be emitted. The controller 110 may comprise a frequency oscillator (not shown), for controlling the frequency of oscillation of the actuator 53, in the case where the latter is of a piezoelectric type.

Advantageously, the controller 110 is supplied by a battery 104 integrated in the inhaler 100.

The inhaler 100 can be activated by pressing a pushbutton 105, which activates the controller 110 for generating emission of the liquid medicament.

The inhaler 100 can moreover comprise a fluidic module 107, constituted by a plurality of channels and/or containers 108, connected to the inlet mouth 54 of the spray device 50 and designed to contain a certain amount of medicament for enabling a recharging of the spray device 50 when, following upon use, the medicament runs out. In turn, the channels and/or containers 108 can be recharged with medicament by the user, when necessary.

Finally, the inhaler 100 may optionally comprise a flowmeter (not shown), set inside or outside the spray device 50, for evaluating the amount of liquid released, and/or a pressure sensor (not shown), for evaluating the level of liquid remaining within the reservoir 51 of the spray device 50.

From an examination of the characteristics of the process of fabrication according to the present disclosure, the advantages that it enables are evident.

In particular the process of fabrication described, according to any one of the embodiments, presents a reduced cost, in so far as the process does not require more than a limited number of process masks, and the membrane of nozzles is produced monolithically starting from a wafer of a standard type, without any need to use processes of a silicon-on-insulator (SOI) type or wafer-to-wafer-bonding processes.

Finally, it is clear that modifications and variations may be made to the process described and illustrated herein, without thereby departing from the sphere of protection of the present disclosure.

For example, the nozzles 14 can be formed at a time different from the one described, for example, after formation of the supply channels 15.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A spray device comprising:
   a reservoir having an inner chamber configured so as to contain a fluid substance; and
   an emission structure coupled to the reservoir for emission of the fluid, said emission structure including a nozzle membrane that includes:
   a substrate;
   a plurality of supply channels in the substrate;
   a membrane layer that includes a plurality of nozzles respectively aligned in a first direction with a respective supply channel of said plurality of supply channels, each nozzle being in direct communication with the respective supply channel; and
   a plurality of guide channels on opposite sides of the respective nozzles with respect to the respective supply channels, each nozzle being positioned between the respective guide channel and the respective supply channel, each supply channel being configured to supply a portion of the fluid to the respective nozzle, each nozzle being configured to output the fluid supplied by the respective supply channel, and each guide channel being configured to guide the fluid output from the respective nozzle, wherein each nozzle has a smaller diameter than the respective guide channel and respective supply channel.

2. The spray device of claim 1, wherein said membrane layer is distinct from said substrate.

3. The spray device of claim 1, wherein the substrate is made of a first material and the membrane layer is made of a second material, the first material being different from the second material or the first and second materials are a same material in different crystalline states.

4. The spray device according to claim 3, wherein said first material is monocrystalline silicon and said second material is polysilicon.

5. The spray device of claim 1, further comprising;
an inlet mouth coupled to the inner chamber to enable filling the reservoir; and
an actuator coupled to the reservoir and configured to cause ejection of the fluid from the reservoir.

6. The spray device of claim 5, wherein the actuator is a piezoelectric actuator.

7. The spray device of claim 1, wherein the supply channels extend lengthwise in a direction that is substantially perpendicular to a face of the substrate.

8. The spray device of claim 1, further comprising anchorages directly coupling at least a portion of the membrane layer to the substrate.

9. An inhaler, comprising:
a controller configured to control a release of a fluid; and
a spray device that includes:
a fluid reservoir having an inner chamber configured to store the fluid; and
an emission structure coupled to the reservoir for emission of the liquid substance, said emission structure including a nozzle membrane that includes:
a substrate;
a plurality of supply channels in the substrate;
a membrane layer that includes a plurality of nozzles respectively aligned in a first direction with a respective supply channel of said plurality of supply channels, each nozzle being in direct communication with the respective supply channel; and
a plurality of guide channels on opposite sides of the respective nozzles with respect to the respective supply channels, each nozzle being positioned between the respective guide channel and the respective supply channel, each supply channel being configured to supply a fluid to the respective nozzle, each nozzle being configured to output the fluid supplied by the respective supply channel, and each guide channel being configured to guide the fluid output from the respective nozzle, wherein each nozzle has a smaller diameter than the respective guide channel and respective supply channel.

10. The inhaler of claim 9, further comprising:
a battery to provide energy to the controller; and
a pushbutton to activate control electronics of the controller;
a fluidic module to store a supply of the fluid, the fluidic module being coupled to the fluid reservoir to re-supply the fluid reservoir with the fluid.

11. The inhaler of claim 10, wherein the pushbutton is configured to expose the nozzle membrane when depressed and keep the membrane of nozzles covered when not depressed.

12. The inhaler of claim 9, further comprising;
an inlet mouth coupled to the inner chamber to enable filling the reservoir; and
an actuator coupled to the reservoir and configured to cause ejection of the fluid from the reservoir.

13. The inhaler of claim 12, wherein the actuator is a piezoelectric actuator.

14. The inhaler of claim 9, wherein the supply channels extend lengthwise in a direction that is substantially perpendicular to a face of the substrate.

15. The inhaler of claim 9, further comprising anchorages directly coupling at least a portion of the membrane layer to the substrate.

16. A nozzle membrane, comprising:
a substrate;
a plurality of supply channels in the substrate;
a membrane layer including a plurality of nozzles respectively aligned in a first direction with a respective supply channel of said plurality of supply channels, each nozzle being in direct communication with the respective supply channel; and
a plurality of guide channels on opposite sides of the respective nozzles with respect to the respective supply channels, each nozzle being positioned between the respective guide channel and the respective supply channel, each supply channel being configured to supply a fluid to the respective nozzle, each nozzle being configured to output the fluid supplied by the respective supply channel, and each guide channel being configured to guide the fluid output from the respective nozzle , wherein each nozzle has a smaller diameter than the respective guide channel and respective supply channel.

17. The nozzle membrane of claim 16, wherein the supply channels extend lengthwise in a direction that is substantially perpendicular to a face of the substrate.

18. The nozzle membrane of claim 17, further comprising anchorages that directly couple at least a portion of the membrane layer to the substrate.

19. The nozzle membrane of claim 16, further comprising;
an inlet mouth coupled to the inner chamber to enable filling the reservoir; and
an actuator coupled to the reservoir and configured to cause ejection of the fluid from the reservoir.

20. The nozzle membrane of claim 19, wherein the actuator is a piezoelectric actuator.

* * * * *